US008843336B2

(12) United States Patent
Cain

(10) Patent No.: US 8,843,336 B2
(45) Date of Patent: Sep. 23, 2014

(54) TRIGGER EVENT DETECTION APPARATUS AND METHOD THEREFOR

(75) Inventor: Peter Cain, Midlothian (GB)

(73) Assignee: Agilent Technologies, Inc., Santa Clara, CA (US)

( * ) Notice: Subject to any disclaimer, the term of this patent is extended or adjusted under 35 U.S.C. 154(b) by 769 days.

(21) Appl. No.: 12/235,248

(22) Filed: Sep. 22, 2008

(65) Prior Publication Data

US 2009/0082982 A1 Mar. 26, 2009

(30) Foreign Application Priority Data

Sep. 21, 2007 (GB) .................................. 0718442.7

(51) Int. Cl.
*G01R 23/16* (2006.01)
*G01R 29/00* (2006.01)
*G01R 13/02* (2006.01)
*G01N 29/46* (2006.01)
*G06F 17/14* (2006.01)

(52) U.S. Cl.
CPC ............ *G01R 13/0254* (2013.01); *G01N 29/46* (2013.01); *G01R 23/16* (2013.01); *G06F 17/14* (2013.01)
USPC .............................................. 702/77; 702/73

(58) Field of Classification Search
CPC ........ G01R 23/16; G01R 29/02; G01R 23/00; G06F 17/141; G06F 17/14; G01N 29/46; G06G 7/1921
USPC ...................................................... 702/73, 77
See application file for complete search history.

(56) References Cited

U.S. PATENT DOCUMENTS

| 6,850,735 | B2 * | 2/2005 | Sugar et al. ................ 455/67.11 |
| 7,116,943 | B2 * | 10/2006 | Sugar et al. ................ 455/67.11 |
| 7,227,349 | B2 * | 6/2007 | Kirkpatrick .............. 324/754.07 |
| 7,352,167 | B2 * | 4/2008 | Sullivan et al. ........... 324/121 R |
| 7,471,652 | B2 * | 12/2008 | Bernard et al. ................ 370/310 |
| 7,782,235 | B1 * | 8/2010 | Velazquez ..................... 341/118 |
| 2003/0224741 | A1 * | 12/2003 | Sugar et al. ................ 455/115.1 |
| 2004/0203826 | A1 * | 10/2004 | Sugar et al. ................ 455/452.1 |
| 2005/0002473 | A1 | 1/2005 | Kloper et al. |
| 2006/0025947 | A1 | 2/2006 | Earls |
| 2006/0133263 | A1 * | 6/2006 | Bernard et al. ............... 370/210 |
| 2007/0053620 | A1 * | 3/2007 | Mizuno ......................... 384/240 |

FOREIGN PATENT DOCUMENTS

| EP | 1672376 A1 | 6/2006 |
| WO | 03090376 A1 | 10/2003 |
| WO | 2007056677 A2 | 5/2007 |

OTHER PUBLICATIONS

Great Britain Search Report dated Dec. 3, 2007.

* cited by examiner

*Primary Examiner* — Michael Nghiem

(57) ABSTRACT

A method of detecting a trigger event includes receiving an input signal for analysis. The received input signal is used to generate first data corresponding to sequential sets of spectral output data sets, at least some of the spectral output data sets corresponding to sample points in time acquired from the input signal as the input signal changes with time. At least part of the first data is then compared with second data, the second data corresponding to a predetermined sequential set of signature spectral data sets corresponding to a time-varying spectrum associated with a trigger event. A trigger signal is then generated in response to a change in a state of match between the at least part of first and second data.

17 Claims, 4 Drawing Sheets

TRIGGER EVENT DETECTION APPARATUS AND METHOD THEREFOR

This application claims priority from Great Britain Patent Application, No. GB 0718442.7 filed on 21 Sep. 2007, which is incorporated by reference in its entirety.

BACKGROUND

The present invention relates to a trigger event detection apparatus of the type that, for example, receives, when in use, an input signal and analyses the input signal in order to detect a trigger event. The present invention also relates to a method of detecting a trigger event of the type that, for example, receives an input signal and analyses the input signal in order to detect the trigger event.

In the field of Radio Resource Management, a Radio Frequency (RF) signal is known to possess a number of characteristics, for example: power, duration, modulation, and space-time coding format. One or more of the characteristics are dynamic and so are changeable. Radio Resource Management, generally speaking, is the practice of optimisation of performance of an RF system by varying one or more of the characteristics.

In order to understand whether the RF system is responding correctly and effectively to changes in an RF environment in which the RF system operates, it is necessary to trigger a measurement instrument on a channel event to which a change in the one or more characteristics responds. A number of causes of the channel event exist, for example fading, interference and/or an error in the RF system. In this respect, certain events are infrequent or sporadic and so it is not possible always to predict when such events will occur and/or the exact nature of such events.

It is known to trigger the measurement instrument based upon RF level and/or frequency criteria, and such criteria allows some signals to be identified for analysis. However, such criteria are not always able to identify a difference in signal type where, for example, modulation type is a distinguishing factor between wanted and unwanted signals to be captured for analysis. For example, a Wireless Local Area Network (WLAN) Access Point, operating in accordance with a communications standard, such as, the Institute of Electronic and Electrical Engineers (IEEE) 802.11g standard, can switch between Direct Sequence Spread-Spectrum (DSSS) modulation and Orthogonal Frequency Division Multiplexing (OFDM) modulation on a same frequency depending upon performance of an RF channel and network operation. Also, the WLAN Access Point uses different types of burst in order to achieve performance of certain network activities. Changes in such characteristics (and others) are not predictable, and not readily detectable for triggering purposes, using existing techniques described above.

Demodulation of an RF signal can be used to provide triggers, but use of demodulation is technology specific and also carries a processing overhead and time penalty when implemented. Furthermore, use of demodulation may not work if the RF signal cannot be demodulated due to one or more errors in the way the RF signal was generated.

SUMMARY

According to a first aspect of the present invention, there is provided a method of detecting a trigger event, comprising: receiving an input signal for analysis; generating first data corresponding to energy of a frequency content of the input signal as the input signal changes with time; comparing at least part of the first data with second data, the second data corresponding to a predetermined time-varying spectrum associated with the trigger event; and generating a trigger signal in response to a detection of a change in state of match between the at least part of the first and the second data.

The state of match may be a discrete state. The state of match may comprise one of a matched state and an unmatched state. The state of match may be the matched state of the unmatched state at a given point in time.

The match between the first and the second data may be a relationship assessed with respect to energy distributed over frequency and time.

The method may further comprise: sampling the input signal; and using the samples of the input signal to generate the first data corresponding to the energy of the frequency content of the input signal as the input signal changes with time.

The method may further comprise: conditioning the input signal prior to generating the first data.

The conditioning may comprise down-converting the input signal. The conditioning may comprise amplitude scaling the input signal. The down conversion may be to baseband.

The conditioning may comprise: converting the input signal from an analogue domain to a digital domain.

The input signal may be in the time domain, and generating the first data comprises: converting a number of the samples of the input signal to the frequency domain. Converting the samples of the input signal to the frequency domain may comprise: performing Fourier Transforms on the number of the samples of the input signal. The Fourier Transform may be a Fast Fourier Transform (FFT).

The method may further comprise: normalising the number of the converted samples of the input signal.

The method may further comprise: truncating the number of the converted samples of the input signal in order to mitigate noise.

Comparing the at least part of the first data with the second data may comprise: pattern matching the at least part of the first data with the second data.

Granularity of the match between the at least part of the first signal and the second signal may be configurable.

Generating the first data corresponding to the energy of the frequency content of the input signal as the input signal changes with time may be configurable with respect to one or more of: a duration of a Fourier Transform, a window function, a proportion of a duration associated with the second data, and/or a dynamic range of the input signal.

According to a second aspect of the present invention, there is provided a computer program element comprising computer program code means to make a computer execute the method as set forth above in relation to the first aspect of the invention.

The computer program element may be embodied on a computer readable medium.

According to a third aspect of the present invention, there is provided a trigger event detection apparatus, comprising: an input for receiving an input signal to analyse; a data generator for generating first data corresponding to energy of a frequency content of the input signal as the input signal changes with time; a comparator for comparing at least part of the first data with second data, the second data corresponding to a predetermined time-varying spectrum associated with a trigger event; and a trigger signal generator for generating a trigger signal in response to detecting a change in a state of match between the at least part of the first and the second data.

According to a fourth aspect of the present invention, there is provided a signal analyser comprising the trigger event detection apparatus as set forth above in relation to the third aspect of the invention.

It is thus possible to provide an apparatus and method that enabled detection of a trigger event based upon variation of spectrum with time. Consequently, the apparatus and method is technology-independent and so does not require demodulation of the input signal in order to detect the trigger event. It is thus also possible to provide early adaptation, in the lifecycle of a new technology, of the apparatus and method to detect a new trigger event. The apparatus can also be used as a general-purpose tool, because the apparatus is not specific to any particular communications technology.

At least one embodiment of the invention will now be described, by way of example only, with reference to the accompanying drawings, in which:

DETAILED DESCRIPTION

Figure 1:
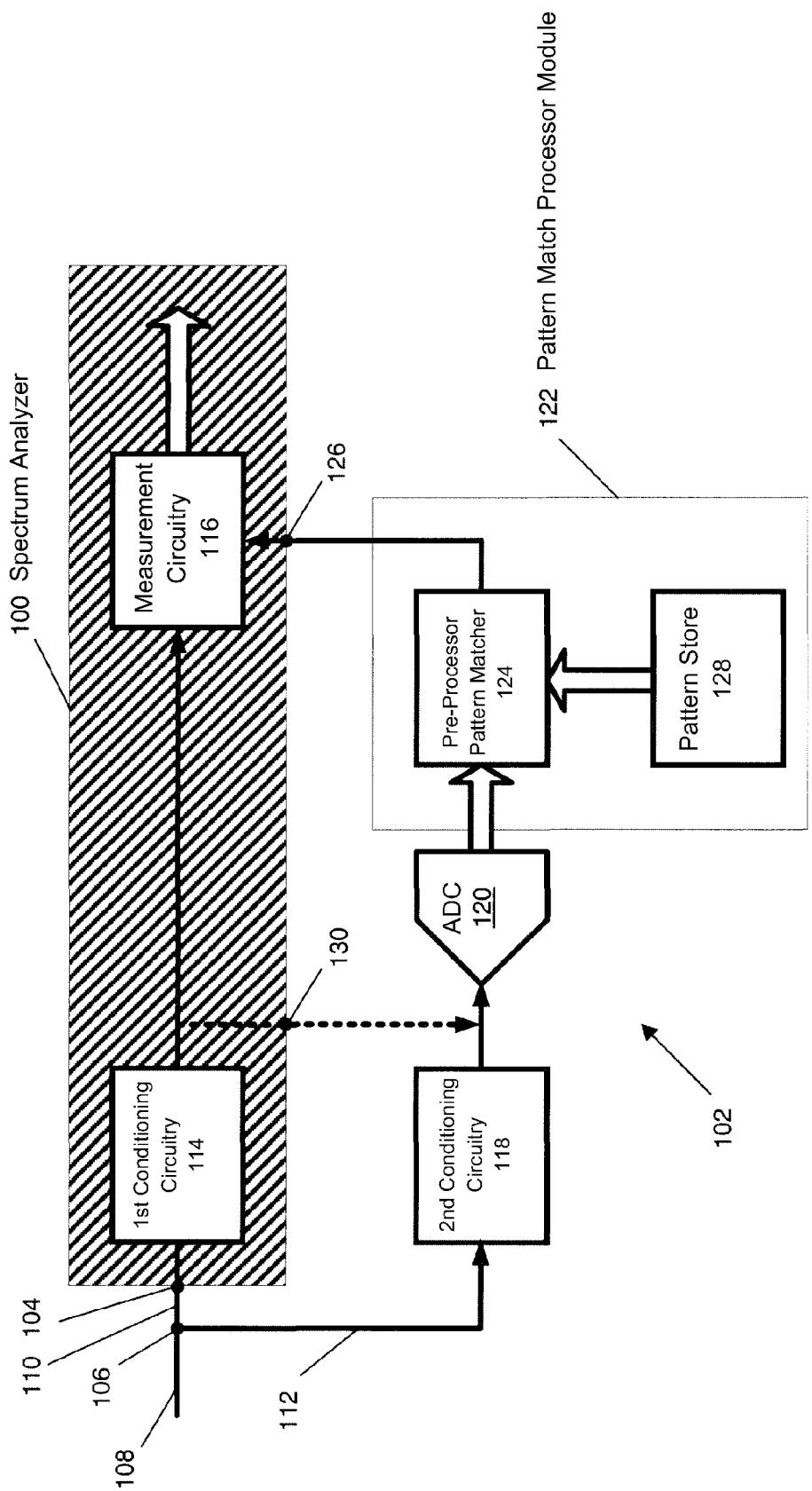
FIG. 1 is a schematic diagram of an apparatus constituting an embodiment of the invention.

Throughout the following description identical reference numerals will be used to identify like parts.

Referring to FIG. 1, a signal analyser, for example a spectrum analyser 100, such as an E4440A PSA Spectrum Analyzer available from Agilent Technologies, Inc., is coupled to a trigger event detection apparatus 102. Of course, the trigger event detector apparatus 102 can be an internal module of the spectrum analyser 100. However, for the sake of clarity of explanation of this embodiment, the trigger event detector apparatus 102 is being described herein as external to the spectrum analyser 100. Indeed, such a configuration can also be employed in any event.

In this example, employing the external trigger event detector apparatus 102, a power splitter 106 has an input path 108 for receiving an input signal (not shown) to be monitored, a primary output path 110 coupled to an RF input port 104 of the spectrum analyser 100 and a secondary output path 112 in order to tap off a proportion of the input signal for use in detection of a predetermined event, for example a channel event.

The spectrum analyser 100 comprises, inter alia, first analogue signal conditioning circuitry 114 capable of performing frequency conversion and amplitude ranging on a first proportion of the input signal received at the RF input port 104 via the primary output path 110. An output of the first conditioning circuitry 114 is coupled to a first input of measurement circuitry 116 having an output for obtaining measurement results. The skilled person will appreciate that the spectrum analyser 100 comprises other functional entities that support the measurement process performed by the spectrum analyser 100. However, for the sake of clarity and conciseness, these features have not been described further herein. Although not shown, functionality is provided that uses the output of the measurement circuitry 116 to provide a representation of the measurement results in any suitable manner required depending upon an application employing the spectrum analyser 100.

The secondary output path 112 of the power splitter 106 is coupled to an input of second analogue conditioning circuitry 118 also capable of performing frequency conversion and amplitude ranging on a second proportion of the input signal received via the secondary output path 112. An output of the second analogue conditioning circuitry 118 is coupled to an input of an Analogue-to-Digital Converter (ADC) 120, an output of the ADC 120 being coupled to a pattern match processor module 122. The pattern match processor module 122 comprises a signal pre-processor and pattern matcher 124 having a first input thereof coupled to the output of the ADC 120, an output of the signal pre-processor and pattern matcher 124 being coupled to a trigger input 126 of the spectrum analyser 100 that is coupled to a second input of the measurement circuitry 116. A pattern store 128, for example a digital memory, is coupled to a second input of the signal pre-processor and pattern matcher 124.

Figure 2:
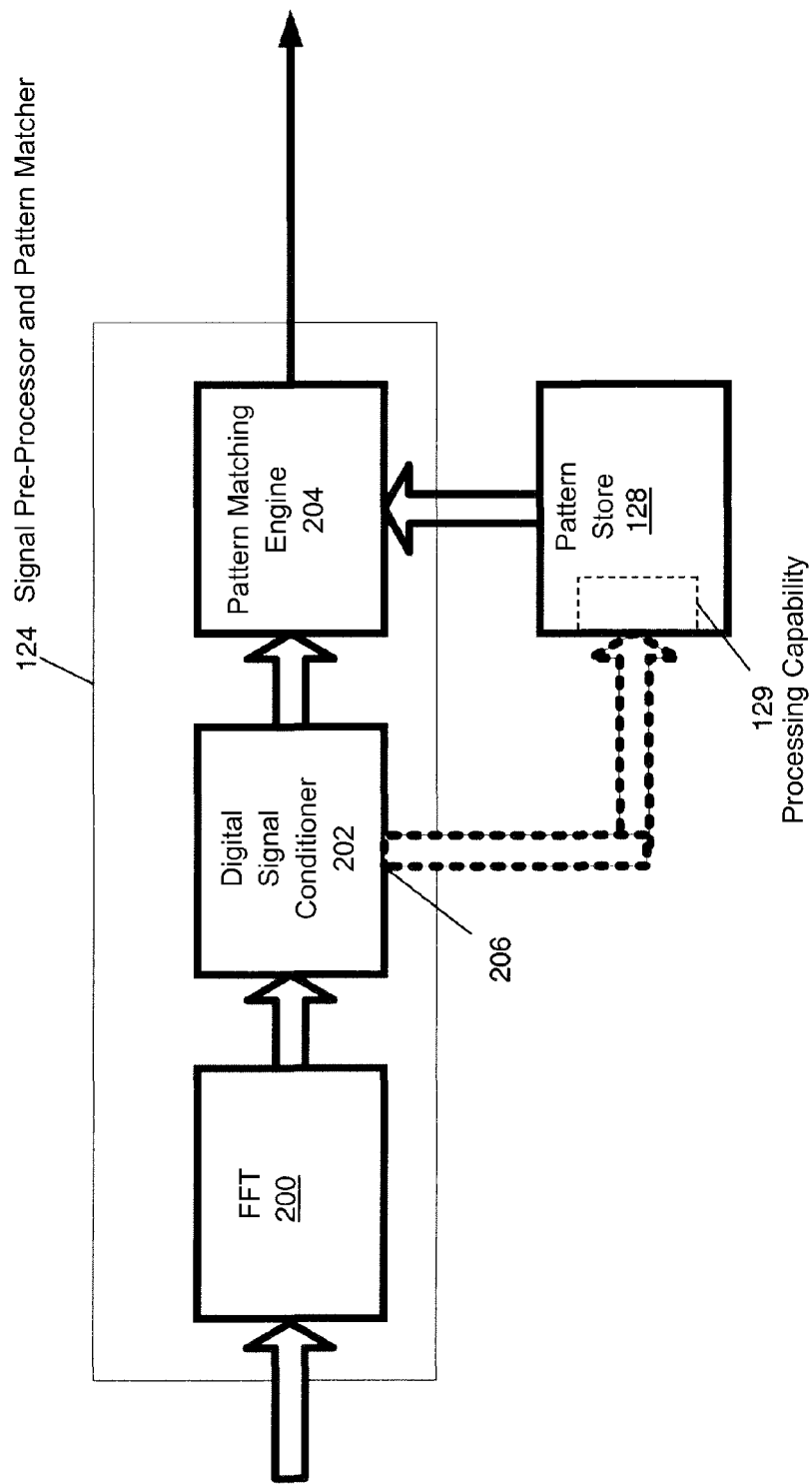
FIG. 2 is a schematic diagram of a part of the apparatus of FIG. 1 in greater detail.

Turning to FIG. 2, the signal pre-processor and pattern matcher 124 comprises a Fast Fourier Transform (FFT) processor 200 coupled to the first input of the signal pre-processor and pattern matcher 124. An output of the FFT processor 200 is coupled to an input of a digital signal conditioner 202, a first output thereof being coupled to a first input of a comparator or pattern matching engine 204.

The pattern matching engine 204 is a functional unit that implements a pattern-matching algorithm in order to determine a matched state between two input patterns and changes with respect to the matched state. One known manner for determining the match is by determining a correlation between the two input patterns. However, the skilled person will appreciate that other techniques can be employed, the exact technique being, in this example, dependent upon processing speed demands. In this example, the two input patterns are sets of data corresponding to energy of a frequency content of signals being compared as the signals being compared change with time. As mentioned above, the algorithm employed by the pattern matching engine 204 can be any suitable algorithm available to determine the above-mentioned match. In this example, the algorithm is configurable in relation to accuracy of match constituting the matched state between the two sets of data being compared and/or resolution/granularity/accuracy tolerance of match.

The pattern store 128 stores sets of signature spectral data sets corresponding to trigger events. A trigger event is a change in relation to the input signal, for example a channel event that is sought, for example, for diagnostic purposes. A set of signature spectral data sets characterises the trigger event and each set is used to identify the associated trigger event. In this respect, each set of signature spectral data sets is a predefined or a pre-stored set of data corresponding to a time-varying spectrum, detection of the time-varying spectrum being indicative of the occurrence of the trigger event associated with the time-varying spectrum. The pattern store 128 stores the sets of signature spectral data sets as a look-up table, though it should be appreciated that other suitable data storage and access techniques can be employed. The pattern store 128 can be populated by uploading pre-defined, for example obtained by simulation or defined using a graphically-driven, or other, user interface, sets of signature spectral data sets. One or more set of signature spectral data sets can also, or alternatively, be obtained by prior waveform capture of a time-varying spectrum.

A second input of the pattern matching engine 204 is coupled to the pattern store 128 via the second input of the signal pre-processor and pattern matcher 124. Where waveform capture is implemented, the digital memory 128 is augmented with a processing capability 129 and the processing capability 129 is coupled to the digital signal conditioner 202 via an optional second output 206 coupled to an input of the pattern store 128 to support the prior waveform capture mentioned above for populating the pattern store 128.

Figure 3:
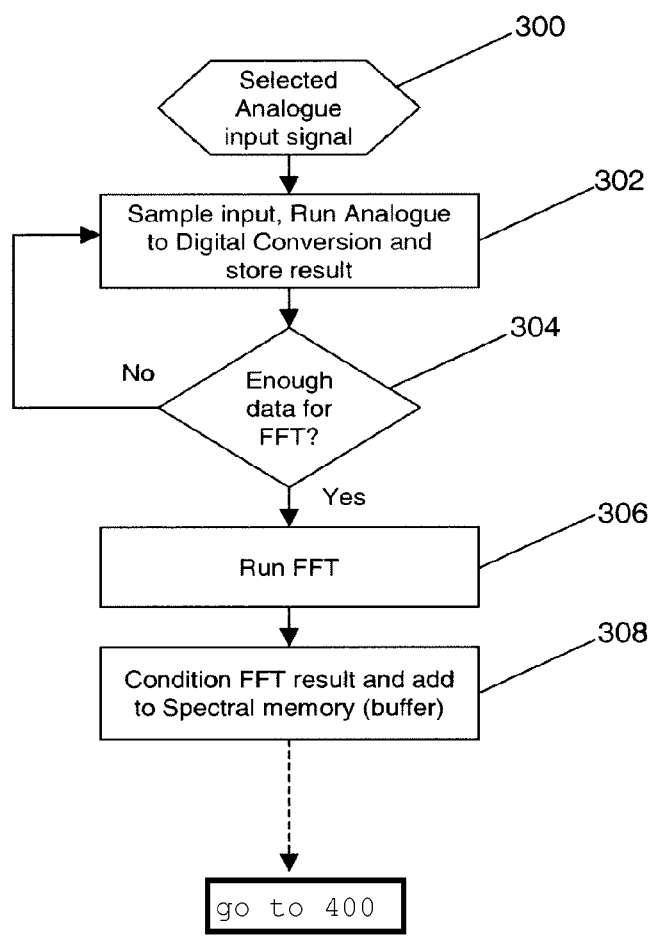
FIGS. 3 and 4 are flow diagrams of parts of a method employed by the apparatus of FIG. 1.

In operation (FIGS. 3 and 4), the input signal is received from a Device Under Test (DUT) via the input path 108. A proportion of the input signal is tapped off by the power splitter 106 and follows (Step 300) the secondary output path 112, the remaining proportion of the input signal being received at the RF input port 104 of the spectrum analyser 100, whereupon the remaining proportion of the input signal is subjected to processing appropriate for testing the DUT. As the skilled person will appreciate, the detail of the processing can vary greatly depending upon the testing being undertaken and so detail of the testing is not relevant to an explanation of the operation of the above-described apparatus. However, it should be noted that a trigger signal is awaited as part of the processing of the remaining proportion of the input signal.

The proportion of the input signal tapped off (hereinafter referred to as the "tapped signal") by the power splitter 106 is an analogue signal that is subjected to conditioning. In this example, the tapped signal is down-converted to a frequency that the ADC 120 is able to process, for example a baseband frequency, and then subjected to amplitude ranging in order to scale the tapped signal to within an amplitude range that the ADC 120 is able to process. The ADC 120 thus receives a continuous tapped conditioned analogue signal that is then sampled and converted (Step 302) from the analogue domain to the digital domain by the ADC 120. The digitised tapped signal generated by the ADC 120 is then stored in a first buffer (not shown). In this example, the ADC 120 continuously samples the conditioned tapped signal at a rate sufficient to capture the full information bandwidth of the conditioned tapped signal, for example at the Nyquist sampling rate.

The FFT processor 200 monitors the state of the first buffer in order to determine (Step 304) when the first buffer contains a sufficient amount of data for the FFT processor 200 to be able to generate a spectral output data set by converting (Step 306) the digitised tapped signal samples from the time domain to the frequency domain. To generate the spectral output data set, the FFT processor 200 employs any suitable Fourier Transform algorithm, for example as available as a library item from a Field Programmable Gate Array (FPGA) supplier. The spectral output data is then subjected to conditioning (Step 308) in the digital domain by the digital signal conditioner 202, for example the dynamic range of the spectral output data is modified to normalise the spectral output data, and the spectral output data is truncated and/or averaged over time in order to mitigate the effects of noise. If desired, the spectral output data generated by the FFT processor 200 can generate the spectral output data based upon sets of the sequential samples that overlap in time. By use of overlapping ranges of input data, the resolution of the spectral output data generated by the FFT processor 200 can be improved. The FFT processor 200 can more generally be referred to as a data generator for generating first data corresponding to energy of a frequency content of the input signal as the input signal changes with time.

Due to the continuous nature of the input signal whilst the DUT is generating the input signal, the FFT processor 200 generates sequential sets of spectral output data sets, one for each sample obtained from the ADC 120. The digitally conditioned spectral output data sets are buffered (Step 308) in a second buffer (not shown) for subsequent comparison.

Whilst the second buffer is filling with conditioned sets of spectral output data sets, the content of the second buffer is made available to the pattern matching engine 204.

Figure 4:
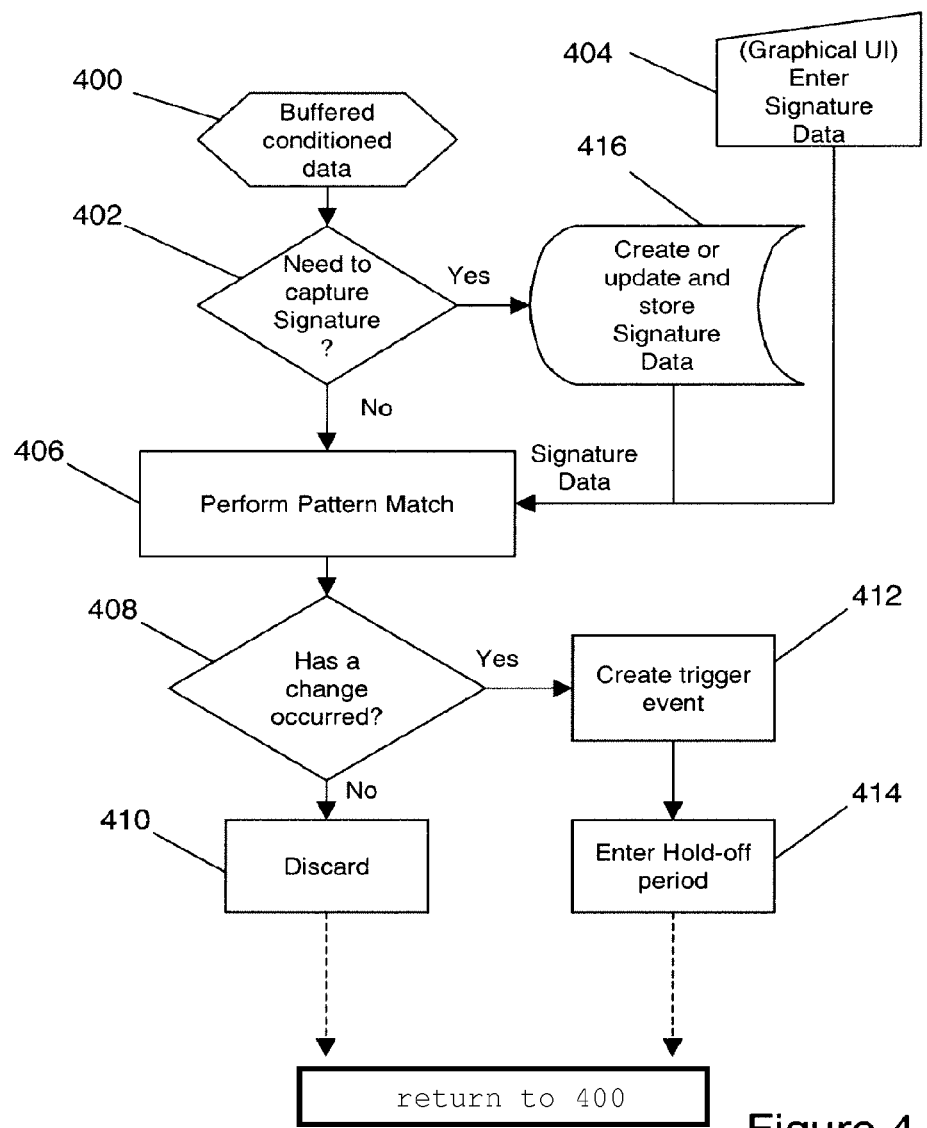

Referring to FIG. 4, the pattern matching engine 204 has access (Step 400) to the second buffer as mentioned above. The pattern matching engine 204 also determines (Step 402) whether a trigger event has been identified for detection. In this example, a user identifies and selects a trigger event to be detected in advance of, or during, testing using a suitable user interface provided (404) and, responsive to this selection, the pattern matching engine 204 initially obtains the sequential set of signature spectral data sets corresponding to the trigger event selected to identify the event that necessitates generation of a trigger signal so that the spectrum analyser 100 can properly measure one or more characteristics of the input signal associated with the trigger event. As will be described in a second embodiment later herein, an alternative technique exists for generating the sequential set of signature data sets.

The pattern matching engine 204 then compares (Step 406) a number of the sequential sets of spectral output data sets with the selected sequential set of signature spectral data sets in order to determine (Step 408) a match between the two sequential sets of data. If a match is not deemed to exist by the algorithm employed by the pattern matching engine 204, the pattern matching engine 204 then discards (Step 410) the number of sequential sets of spectral data sets and repeats the above pattern matching process with a subsequent sequential set of spectral output data sets and repeats the comparison (Step 406). The above pattern match determination process is repeated until the pattern matching engine 204 finds a match between the selected sequential set of spectral data sets and the sequential set of signature spectral data sets. Once a match has been found, the pattern matching engine 204 generates (Step 412) a trigger signal, using a trigger signal generator 205 as shown in FIG. 2, that is received by the spectrum analyser 100. The pattern matching engine 204 then implements a hold-off period (Step 414) before selecting another subsequent set of spectral data sets and the above pattern matching process is repeated until measurement is complete.

It should be appreciated that references herein to "match" of data relate to a determination of a state of match. The match between the two sequential sets of data need not be identical and a degree of match or strength of relationship between two sets of data being compared can be selected.

In another embodiment, the pre-stored set of data corresponding to the time-varying spectrum indicative of the occurrence of the trigger event is obtained (Step 416) by use of the processing capability 129 of the augmented pattern store 128 mentioned above. In this respect, the pattern store 128 is arranged to monitor the second output 206 of the digital signal conditioner 202, the conditioned spectral output data corresponding, in this example, to a repeating data set. A user configures the processing capability 129 of the pattern store 128 to monitor a desired number of cycles of the repeating signal. The conditioned spectral output data for the repeating signal is then averaged in order to mitigate the repeating nature of the repeating data set and noise and then stored by the pattern store 128 as an "expected pattern". The pattern matching engine 204 then obtains the expected pattern recorded, in the same manner as described above in relation to the previous embodiment. The process of pattern matching (Step 406) is then performed, but to identify changes (Step 408) in the input signal that, when spectrum analysed, deviate from the expected pattern; a trigger signal is generated (Step 412) if the deviation from the expected pattern is detected. The generation of the trigger signal is, in this example, dependent upon deviation from the expected pattern from the state of match above a threshold change value. The threshold change value hence serves as a sensitivity setting. For example, a slow deviation of the conditioned spectral output data from the expected pattern may not be of interest to the user. Once the trigger signal has been generated, the pattern match engine 204 implements (Step 414) the hold-off period.

The skilled person should appreciate that the pattern matching process and/or signal conditioning can additionally or alternatively be configured by a user in the following exemplary ways. One or more of the following parameters can be user-defined: the duration of the FFT, the window function used to determine a shape of a filter in the time and frequency domains and hence a rejection level of signals in adjacent frequency bins, a proportion of the duration of a signature data set used for pattern matching, and/or a dynamic range of the signature data set.

The spectrum analyser 100 responds to the trigger signal generated in accordance with the normal operating practice of the spectrum analyser 100 in relation to trigger signals. When used in conjunction with a so-called "pre-triggering" function of the spectrum analyser 100, the sequential set of signature spectral data sets can be used to determine complete RF interaction of the DUT around specifically selected events.

In this example, the functionality provided to generate the trigger signal is implemented in hardware using an FPGA. However, the skilled person will appreciate that any other suitable implementation can be employed, provided a sufficiently high processing speed can be provided.

Although not specifically mentioned above, the first analogue conditioning circuitry 114 of the spectrum analyser 100 can perform signal conditioning in an analogous manner to that described above in relation to the second analogue conditioning circuitry 118. Consequently, the down-conversion and ranging functionality of the spectrum analyser 100 can be used instead of the second analogue conditioning circuitry 118, thereby obviating the need for the second analogue conditioning circuitry 118 and the power splitter 106. In such an embodiment, the output of the first analogue conditioning circuitry 114 is coupled to the input of the ADC 120 via a tapped output port 130 with which the spectrum analyser 100 provided. The first analogue conditioning circuitry 114 down-converts the input signal to an Intermediate-Frequency (IF) and scales the down-converted input signal. In such an example, the ADC 120 is specified so as to be able to process signals at the IF, where the IF bandwidth is sufficiently wide to capture any content of the input signal that can constitute useful trigger information.

Alternative embodiments of the invention can be implemented as a computer program product for use with a computer system, the computer program product being, for example, a series of computer instructions stored on a tangible data recording medium, such as a diskette, CD-ROM, ROM, or fixed disk, or embodied in a computer data signal, the signal being transmitted over a tangible medium or a wireless medium, for example, microwave or infrared. The series of computer instructions can constitute all or part of the functionality described above, and can also be stored in any memory device, volatile or non-volatile, such as semiconductor, magnetic, optical or other memory device.

The invention claimed is:

1. A method of detecting a trigger event, comprising:
   receiving an input signal for analysis;
   splitting the input signal into an analog first portion and an analog second portion of the input signal;
   digitizing the analog second portion of the input signal;
   generating first data corresponding to sequential sets of spectral output data sets from the digitized second portion, at least some of the spectral output data sets corresponding to sample points in time acquired from the digitized second portion of the input signal as the input signal changes with time;
   comparing at least part of the first data with second data, the second data corresponding to a predetermined sequential set of signature spectral data sets corresponding to a time-varying spectrum associated with the trigger event; and
   generating a trigger signal for triggering processing of the analog first portion of the input signal in response to a detection of a change in state of match between the at least part of the first data and the second data.

2. The method as claimed in claim 1, wherein the match between the first and the second data is a relationship assessed with respect to energy distributed over frequency and time.

3. The method as claimed in claim 1, further comprising:
   sampling the analog second portion of the input signal; and
   using the samples of the analog second portion of the input signal to generate the first data corresponding to sequential sets of spectral output data sets of the input signal as the input signal changes with time.

4. The method as claimed in claim 3, wherein the input signal is in the time domain, and generating the first data comprises:
   converting a number of the samples of the digitized second portion of the input signal to the frequency domain.

5. The method as claimed in claim 4, wherein converting the samples to the frequency domain comprises:
   performing Fourier Transforms on the number of the samples of the digitized second portion of the input signal.

6. The method as claimed in claim 5, wherein generating the first data corresponding to sequential sets of spectral output data sets as the input signal changes with time is configurable with respect to one or more of: a duration of a Fourier Transform, a window function, a proportion of a duration associated with the second data, and/or a dynamic range of the input signal.

7. The method as claimed in claim 4, further comprising:
   normalising the number of the converted samples of the input signal.

8. The method as claimed in claim 4, further comprising:
   truncating the number of the converted samples of the input signal in order to mitigate noise.

9. The method as claimed in claim 1, further comprising:
   conditioning the analog second portion of the input signal prior to generating the first data.

10. The method as claimed in claim 9, wherein the conditioning comprises:
    down-converting the analog second portion of the input signal.

11. The method as claimed in claim 10, wherein the down conversion is to baseband.

12. The method as claimed in claim 1, wherein comparing the at least part of the first data with the second data comprises:
    pattern matching the at least part of the first data with the second data.

13. The method as claimed in claim 1, wherein granularity of the match between the at least part of the first signal and the second signal is configurable.

14. A non-transitory computer readable medium comprising computer program code to make a computer execute the method as claimed in claim 1.

15. A trigger event detection apparatus for detecting a trigger event in an input signal, the input signal being split into an analog first portion and an analog second portion, comprising:
- an analogue-to-digital converter (ADC) for receiving and digitizing the analog second portion of the input signal;
- a data generator for generating first data corresponding to sequential sets of spectral output data sets, at least some of the spectral output data sets corresponding to sample points in time acquired from the digitized second portion of the input signal as the input signal changes with time;
- a pattern match processor module for comparing at least part of the first data with second data, the second data corresponding to an expected sequential set of signature spectral data sets corresponding to a time-varying spectrum, and for generating a trigger signal in response to detecting a deviation of the first data from the second data, wherein the trigger signal is provided to measurement circuitry to trigger processing of the analog first portion of the input signal.

16. The trigger event detection apparatus of claim 15, wherein the pattern match processor module comprises:
- a pattern store for storing the expected sequential set of signature spectral data provided as the second data; and
- a pattern matcher for sampling the digitized second portion of the input signal, generating the first data, and comparing the first data with the second data from the pattern store to determine a matched state according to a pattern-matching algorithm.

17. The trigger event detection apparatus of claim 15, wherein the trigger event detection apparatus is comprised in a signal analyser.

* * * * *